(12) United States Patent
Ishikawa

(10) Patent No.: US 12,370,071 B2
(45) Date of Patent: Jul. 29, 2025

(54) PELVIS CORRECTION BELT

(71) Applicant: Yasuhiko Ishikawa, Takamatsu (JP)

(72) Inventor: Yasuhiko Ishikawa, Takamatsu (JP)

( * ) Notice: Subject to any disclaimer, the term of this patent is extended or adjusted under 35 U.S.C. 154(b) by 389 days.

(21) Appl. No.: 17/760,591

(22) PCT Filed: Mar. 5, 2020

(86) PCT No.: PCT/JP2020/009408
§ 371 (c)(1),
(2) Date: Mar. 15, 2022

(87) PCT Pub. No.: WO2021/079539
PCT Pub. Date: Apr. 29, 2021

(65) Prior Publication Data
US 2022/0401247 A1    Dec. 22, 2022

(30) Foreign Application Priority Data
Oct. 25, 2019 (JP) .................................. 2019-194207

(51) Int. Cl.
*A61F 5/02* (2006.01)

(52) U.S. Cl.
CPC .................... *A61F 5/028* (2013.01)

(58) Field of Classification Search
CPC .... A61F 5/00; A61F 5/01; A61F 5/012; A61F 5/0104; A61F 5/02; A61F 5/022;
(Continued)

(56) References Cited

U.S. PATENT DOCUMENTS 6,342,044 B1 *  1/2002  Frangi ............... A61F 5/028
                                                  602/65
10,842,660 B1 * 11/2020  Norstrem ........... A61N 1/0484
(Continued)

FOREIGN PATENT DOCUMENTS

JP           3118691 U  *  2/2006
JP       2017-158993 A     9/2017

OTHER PUBLICATIONS

Machine translation of Publication No. JP3118691U created May 14, 2024 from Google Patents [retrieved from URL<https://patents.google.com/patent/JP3118691U/en?oq=JP3118691U] (Year: 2006).*

(Continued)

*Primary Examiner* — Alireza Nia
*Assistant Examiner* — Gina McCarthy
(74) *Attorney, Agent, or Firm* — Muncy, Geissler, Olds & Lowe, P.C.

(57) ABSTRACT

A pelvis correction belt includes a support member (10) and a press member (20). The press member is provided with multiple belt members (22, 24) placed in upper and lower portions and having elasticity in a longitudinal direction, and the belt members (22, 24) press the pelvis by coupling coupling parts (30, 40) of the press member. The pelvis correction belt is further provided with a first pressing auxiliary belt (50) and a second pressing auxiliary belt (60), each of which extends to both left and right sides from the support member (10) and has a combining part (52, 62) on its tip that can combine with one of the coupling parts (40). By combining the combining parts (52, 62) with the coupling parts (30, 40), the first pressing auxiliary belt (50) and the second pressing auxiliary belt (60) respectively press left and right portions on the rear side of the pelvis.

14 Claims, 4 Drawing Sheets

(58) Field of Classification Search
CPC .......... A61F 5/024; A61F 5/026; A61F 5/028; A61F 5/03; A61F 5/05; A61F 5/30; A61F 5/32; A61H 1/006; A61H 1/008; A61H 2201/1623; A61H 2201/1626; A41F 9/002
See application file for complete search history.

(56) References Cited

U.S. PATENT DOCUMENTS

| | | | |
|---|---|---|---|
| 2015/0250634 A1* | 9/2015 | Garth | A61F 5/028 602/19 |
| 2018/0085244 A1* | 3/2018 | Burke | A61F 13/01038 |
| 2019/0374367 A1* | 12/2019 | Devillers | A61F 5/028 |

OTHER PUBLICATIONS

Coffin, Kimberly. What is Bias Tape and How to Use It. 2024. [retrieved on May 16, 2024]. Retrieved from the Internet <URL: https://sweetredpoppy.com/what-is-bias-tape-and-how-to-use-it/ (Year: 2024).*

* cited by examiner (a)

(b)

PELVIS CORRECTION BELT

TECHNICAL FIELD

This invention relates to a pelvis correction belt.

BACKGROUND

Disclosed as a conventional pelvis correction belt in Patent Document 1 is a configuration where one ends of two upper and lower pieces, four in total, of elastic belts are attached to both the left and right sides of a central supporting part in contact with the vicinity of the sacral region of a user, allowing it to be attached to the pelvis by coupling the other ends of the elastic belts with them on the stomach side of the user.

It is set up so that among pressing forces by the four elastic belts, when viewed from the rear of the user, the one placed in the lower right becomes the maximum, the ones placed in the upper right and the lower left become the minimum, and the one placed in the upper left becomes intermediate of them.

RELATED ART DOCUMENTS

Patent Documents

[Patent Doc. 1] JP Laid-Open Patent Application Publication 2017-158993

SUMMARY

Subject(s) to be Solved

Because the above-mentioned conventional pelvis correction belt has the pressing forces by the four elastic belts differ between up and down and between left and right, incorrect angles and distortion of the pelvis can be corrected to improve symptoms such as lower back pain. On the other hand, attaching it to the user's body in a well-balanced manner can be difficult due to differences among the individual pressing forces, which was room for improvement.

Then, the objective of this invention is to offer a pelvis correction belt that can precisely apply desired pressing forces to the user's desired parts while facilitating its attachment to the pelvis.

Means to Achieve the Objective(s)

The objective of the present invention is achieved by a pelvis correction belt having a support member and an elongated press member attached to the support member so as to extend to both left and right sides, wherein the press member is provided with multiple belt members that are placed in upper and lower portions and have elasticity in a longitudinal direction, and has coupling parts each at both ends of the press member, and the belt members press the pelvis with elastic forces by having the support member contact with a rear side of the pelvis and coupling the coupling parts of the press member on a front side of the pelvis, the pelvis correction belt is further provided with a first pressing auxiliary belt and a second pressing auxiliary belt, each of which extends to both the left and right sides from the support member and has a combining part on its tip that can combine with one of the coupling parts, and by combining the combining parts with the coupling parts, the first pressing auxiliary belt and the second pressing auxiliary belt respectively press left and right portions on the rear side of the pelvis.

It is preferred for the pelvis correction belt that the first pressing auxiliary belt and the second pressing auxiliary belt extend to both the left and right sides from different positions of the support member in an up-down direction, and by combining the combining parts with the coupling parts, the first pressing auxiliary belt presses an upper-left portion on the rear side of the pelvis, and the second pressing auxiliary belt presses an lower-right portion on the rear side of the pelvis. In this configuration, it is preferred that a pressing force by the second pressing auxiliary belt is greater than a pressing force by the first pressing auxiliary belt.

The belt member may be provided with a wide protective part on a portion where the belt member is in contact with a lower-right portion on the rear side of the pelvis. The second pressing auxiliary belt may press the pelvis through the protective part.

Advantage(s) of the Invention

This invention can offer a pelvis correction belt that can precisely apply desired pressing forces to the user's desired parts while facilitating its attachment to the pelvis.

PREFERRED EMBODIMENT(S) OF THE INVENTION

Figure 1:
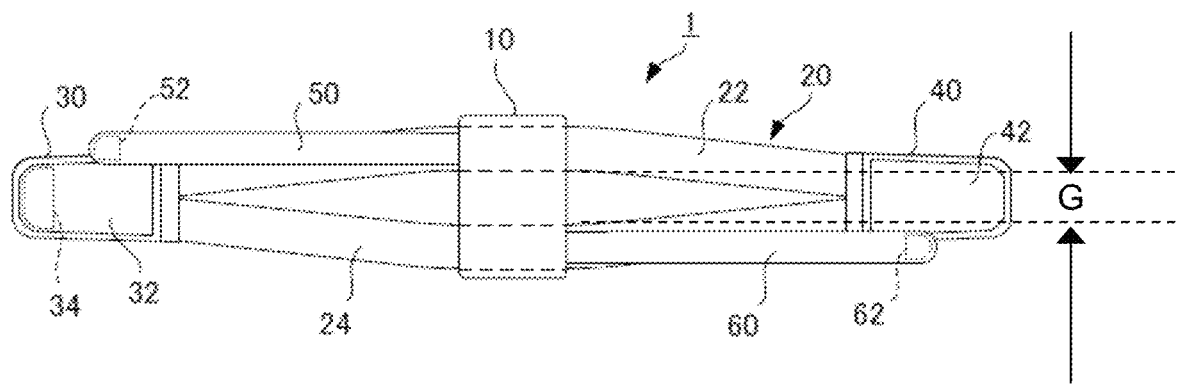
FIG. 1 is a front view of a pelvis correction belt of an embodiment of this invention.
Figure 2:
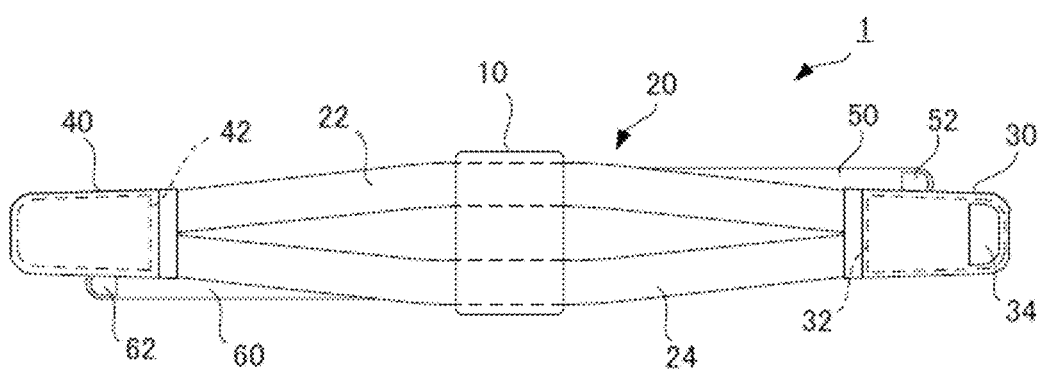
FIG. 2 is a rear view of the pelvis correction belt shown in FIG. 1.

Below, embodiments of this invention are explained referring to attached drawings. FIG. 1 is a front view of a pelvis correction belt of an embodiment of this invention, and FIG. 2 is a rear view of the pelvis correction belt shown in FIG. 1. As shown in FIGS. 1 and 2, the pelvis correction belt 1 is provided with a support member 10 and a press member 20.

The support member 10 is, when a pelvis correction belt 1 is attached to a pelvis, a member in a rectangular plate shape contacting with a part corresponding to the sacrum on the center of the rear side of the pelvis, and is placed so that its longitudinal direction is aligned to the vertical direction (when the user stands up). The support member 10 is preferably made of a non-elastic material and can be formed of fabric, synthetic resin, wood, plaster, or the like for example. When the supporting material 10 is hard, the support member 10 may be covered with a cover member made of cloth, sponge, or the like. The support member 10 of this embodiment is configured by folding a non-elastic fabric in two so as to nip-hold the center of the press member 20 mentioned below.

The press member 20 is formed elongated, placed so as to extend to both the left and right sides of the support member 10, and has coupling parts 30 and 40 at its ends, respectively.

The press member 20 is provided with two belt members 22 and 24 formed of woven fabric, knitted fabric, rubber material, or the like having elasticity in the longitudinal direction. The belt members 22 and 24 are placed in the upper and lower portions of the support member 10, respectively, and their central parts are attached to the support member 10 by sewing, gluing, or the like. As shown in FIG. 1, the belt members 22 and 24 are separated vertically by a gap G. The gap has about a width of one of the belt members 22 and 24. The two belt members 22 and 24 can be divided into the left and right portions of the support member 10 with their ends individually fixed to the support member 10, or can be formed by cutting out the width-direction center of a single belt. The shapes of the belt members 22 and 24 are not particularly limited but can be linear or curved shapes for example.

The one coupling part 30 has a female-type surface fastener 32 installed on the front side exposed to the exterior when attached to the pelvis, and a male-type surface fastener 34 installed on the rear side. Also, the other coupling part 40 has a female-type surface fastener 42 installed on the front side, and by engaging the male-type surface fastener 34 of the coupling part 30 with this female-type surface fastener 42, the coupling parts 30 and 40 can be coupled with each other. Coupling of the coupling parts 30 and 40 can be performed using another detachable coupling means such as snap buttons or hooks than the surface fasteners.

Also, the pelvis correction belt 1 of this embodiment is further provided with a first pressing auxiliary belt 50 and a second pressing auxiliary belt 60. The first pressing auxiliary belt 50 and the second pressing auxiliary belt 60 are formed of a material having elasticity in the longitudinal direction in the same manner as the belt members 22 and 24, and their base ends are attached to the support member 10 so as to extend to both the left and right sides from vertically different positions of the support member 10. Installed on the tips of the first pressing auxiliary belt 50 and the second pressing auxiliary belt 60 are combining parts 52 and 62 that can combine with the coupling part 30, and by combining the combining parts 52 and 62 with the coupling part 30, the first pressing auxiliary belt 50 presses the upper-left portion on the rear side of the pelvis, and the second pressing auxiliary belt 60 presses the lower-right portion on the rear side of the pelvis.

The combining parts 52 and 62 are each made of a male-type surface fastener installed on the rear side of the tip of the first pressing auxiliary belt 50 or the second pressing auxiliary belt 60, and both can engage with the female-type surface fastener 32 of the one coupling part 30. In the same manner as the coupling parts 30 and 40, the combining parts 52 and 62 can also employ another combining means such as snap buttons or hooks that are detachable from the coupling parts 30 and 40.

Figure 3:
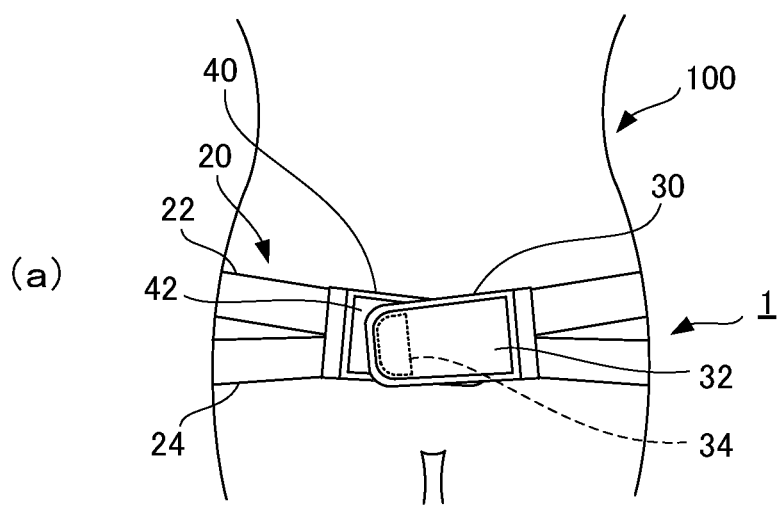
FIG. 3 is a diagram for explaining the method to use the pelvis correction belt shown in FIG. 1.
Figure 3:
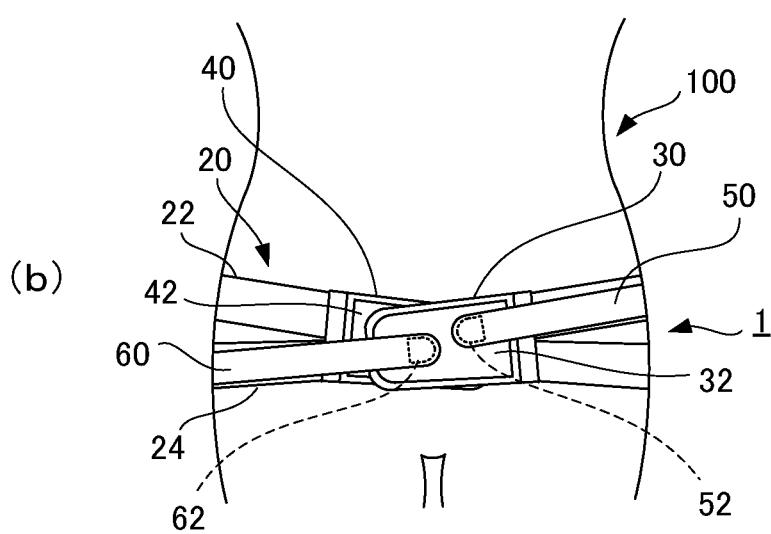

In the pelvis correction belt 1 provided with the above-mentioned configuration, after having the support member 10 contact with the rear side of the user's pelvis, by mutually superimposing the coupling parts 30 and 40 on the front side of the pelvis as shown in FIG. 3(a), the male-type surface fastener 34 of the one coupling part 30 engages with the female-type surface fastener 42 of the other coupling part 40, and the coupling parts 30 and 40 are coupled. Thereby, the pelvis correction belt 1 is attached to the pelvis, and the belt members 22 and 24 of the press member 20 press the upper and lower portions of the pelvis with their elastic forces. The pressing forces applied applies to the pelvis by the belt members 22 and 24 is preferably the same among the left and right and the upper and lower portions (or side) of the support member 10, thereby when the pelvis correction belt 1 is attached, there is no possibility that the pelvis correction belt 1 becomes inclined or shifted relative to the pelvis, allowing it to be easily and precisely attached to the pelvis.

Next, as shown in FIG. 3(b), the combining parts 52 and 62 of the first pressing auxiliary belt 50 and the second pressing auxiliary belt 60 are combined with the female-type surface fastener 32 of the coupling part 30. Thereby, the first pressing auxiliary belt 50 presses the upper-left portion on the rear side of the pelvis through the belt member 22, and the second pressing auxiliary belt 60 presses the lower-right portion on the rear side of the pelvis through the belt member 24. In this manner, the first pressing auxiliary belt 50 and the second pressing auxiliary belt 60 each apply desired pressing forces to desired parts of the pelvis while the press member 20 is pressing the pelvis, which allows correcting distortions of the sacroiliac joints and the lumbosacral joint.

Although the pressing forces applied by the first pressing auxiliary belt 50 and the second pressing auxiliary belt 60 can be the same with each other, the pressing force by the second pressing auxiliary belt 60 is preferably greater than the pressing force by the first pressing auxiliary belt 50. The pressing forces by the first pressing auxiliary belt 50 and the second pressing auxiliary belt 60 can be adjusted by making the expansion and contraction rates of their materials, widths, lengths, thicknesses, shapes, etc. different from each other, and they can be combined as appropriate.

Figure 4:
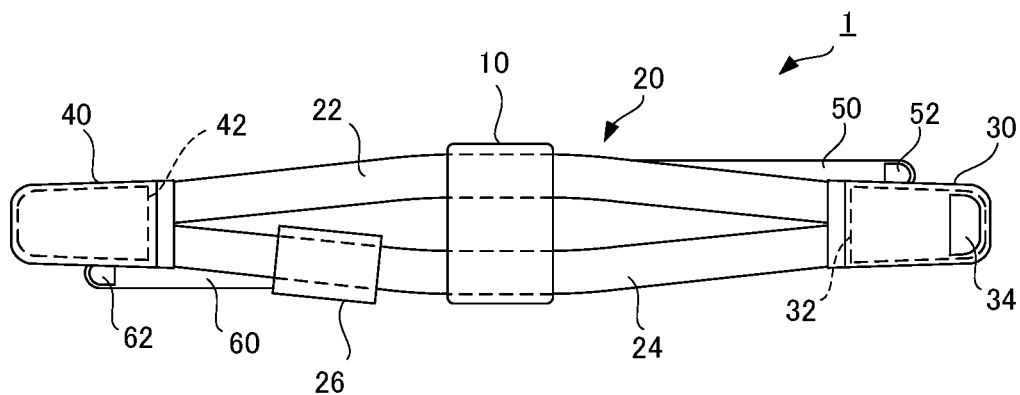
FIG. 4 is a rear view of a pelvis correction belt of another embodiment of this invention.

As shown in FIG. 4, a protective part 26 formed wider than other parts can be installed on the part where the belt member 24 in the lower side of the press member 20 contacts with the rear side of the pelvis so that the second pressing auxiliary belt 60 presses the lower portion of the pelvis through the protective part 26 when attached to the pelvis. Because this configuration allows dispersing the pressing force by the second pressing auxiliary belt 60 by the protective part 26, thereby comfortable wearing feeling can be maintained. The protective part 26 can be a separate cloth or the like from the belt member 24 and attached to the belt member 24, or installed integrally with the belt member 24. Note that in FIG. 4 the same components as in FIG. 1 are assigned the same codes (the same applies in the following figures as well).

Figure 5:
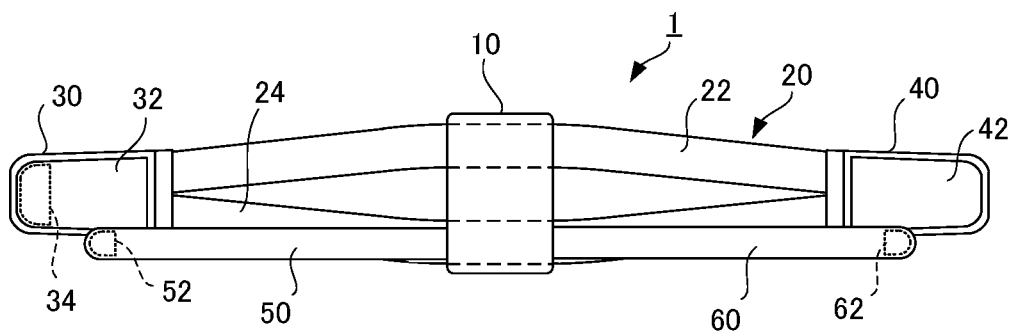
FIG. 5 is a front view of a pelvis correction belt of yet another embodiment of this invention.
Figure 6:
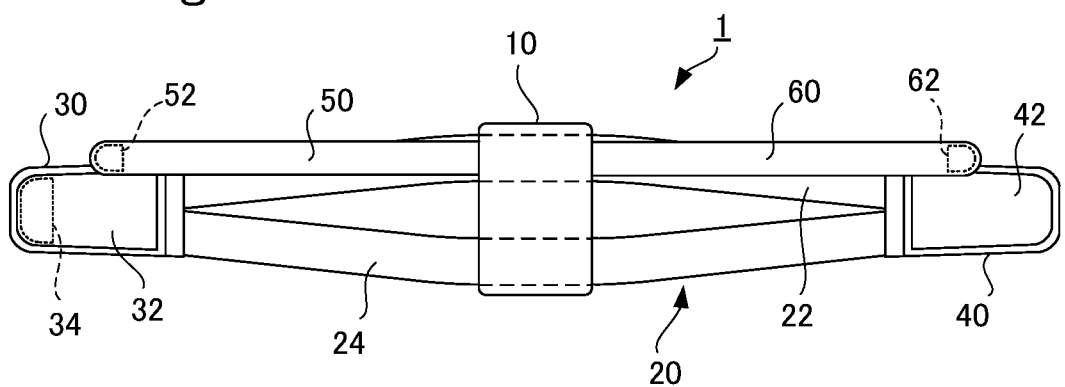
FIG. 6 is a front view of a pelvis correction belt of yet another embodiment of this invention.

In the pelvis correction belt 1 of this embodiment, although the first pressing auxiliary belt 50 and the second pressing auxiliary belt 60 are arranged so as to extend to both the left and right sides from vertically different positions of the support member 10, as shown in FIGS. 5 and 6, they can be arranged so as to extend to both the left and right sides from vertically the same height positions of the support member 10.

In other words, the pelvis correction belt 1 shown in FIG. 5 has the first pressing auxiliary belt 50 and the second pressing auxiliary belt 60 attached to the lower portion of the support member 10 so as to press the lower left and right portions on the rear side of the pelvis, thereby improving an excessive forward tilt of the lumbosacral joint. Also, the pelvis correction belt 1 shown in FIG. 6 has the first pressing auxiliary belt 50 and the second pressing auxiliary belt 60 attached to the upper portion of the support member 10 so as to press the upper left and right portions on the rear side of the pelvis, thereby improving an excessive backward tilt of the lumbosacral joint. The first pressing auxiliary belt 50 and the second pressing auxiliary belt 60 shown in FIGS. 5 and 6 preferably have the same pressing forces.

In any of the above-mentioned embodiments, the first pressing auxiliary belt 50 and the second pressing auxiliary belt 60 preferably press the pelvis through the press member 20. In the pelvis correction belt 1 shown in FIG. 5, the protective part 26 shown in FIG. 4 can be installed on both the left and right sides where the belt member 24 in the lower side of the press member 20 is in contact with the rear side of the pelvis.

LEGENDS

1: pelvis correction belt
10: support member
20: press member
22, 24: belt member
26: protective part
30, 40: coupling part
50: first pressing auxiliary belt
52: combining part
60: second pressing auxiliary belt
62: combining part

What is claimed is:

1. A pelvis correction belt comprising: a support member and an elongated press member attached to the support member so as to extend to both left and right sides such that the press member is configured to wrap a pelvis of a user, wherein the press member is configured with first and second belt members that have elasticity in a longitudinal direction wherein the first and second belt members are placed respectively in upper and lower portions of the support member such that central parts thereof are attached to the support member wherein the first belt member has a width in a width direction, which is perpendicular to the longitudinal direction, and the upper portion and the lower portion of the support member are separated vertically by a gap of about the width of the first belt member, distal ends of the first and second belt members are united, and coupling parts are placed at the distal ends of the first and second belt members, the first and second belt members are configured to press the pelvis with elastic forces when having the support member contact with a rear side of the pelvis, which corresponds to a backbone of the user, and when in use coupling the coupling parts of the press member on a front side of the pelvis, wherein the coupling parts are configured to be coupled by overlapping one another, and one of the coupling parts that is positioned above the other of the coupling parts is defined as a front coupling part, and a surface of the front coupling part that does not face the user is defined as a front surface of the front coupling part, the pelvis correction belt is further provided with a first pressing auxiliary belt and a second pressing auxiliary belt, each of which having a distal end and a base end wherein the distal end is a free tip not fixed to any portion of the pelvis correction belt and has a combining part when the pelvis correction belt wraps the hip, the base end of the first pressing auxiliary belt is attached to the upper portion of the support member so as to be configured to extend from the support member to the left of the user, the base end of the second pressing auxiliary belt is attached to the lower portion of the support member so as to be configured to extend from the support member to the right of the user, and by combining the combining parts of the first pressing auxiliary belt and the second pressing auxiliary belt both with the front surface of the front coupling part, the first pressing auxiliary belt is configured to press an upper-left portion on the rear side of the pelvis through the first belt member, and the second pressing auxiliary belt is configured to press a lower-right portion on the rear side of the pelvis through the second belt member.

2. The pelvis correction belt according to claim 1, wherein a pressing force by the second pressing auxiliary belt is greater than a pressing force by the first pressing auxiliary belt.

3. The pelvis correction belt according to claim 2, wherein the second belt member of the press member is provided with a wide protective part on a portion where the second belt member of the belt members is configured to be in contact with the lower-right portion on the rear side of the pelvis, and the second pressing auxiliary belt presses the pelvis through the protective part.

4. The pelvis correction belt according to claim 1, wherein the combining parts of the first pressing auxiliary belt and the second pressing auxiliary belt are combined with the front surface of the front coupling part using hook and loop fasteners, and the front surface of the front coupling part has one type selected either from the hook fastener or the loop fastener, and the combining parts of the first pressing auxiliary belt and the second pressing auxiliary belt both have the other type of the hook and loop fasteners, different from the front surface of the front coupling part.

5. The pelvis correction belt according to claim 4, wherein the coupling parts of the first and second belt members are coupled using hook and loop fasteners, wherein the coupling part that is positioned behind the front coupling part is defined as a back coupling part, and a surface of the back coupling part that is configured to not face the user is defined a front surface of the back coupling part, the front surface of the back coupling part has the same type of the hook and loop fasteners as the front surface of the front coupling part such that the combining parts of the first pressing auxiliary belt and the second pressing auxiliary belt are able to be combined with the front surface of the back coupling part as well as the front coupling part.

6. The pelvis correction belt according to claim 1, wherein the second belt member of the press member is provided with a wide protective part on a portion where the second belt member of the belt members is configured to be in contact with the lower-right portion on the rear side of the pelvis, and the second pressing auxiliary belt presses the pelvis through the protective part.

7. The pelvis correction belt according to claim 1, wherein the second belt member has the same width as the first belt member.

8. A pelvis correction belt comprising: a support member and an elongated press member attached to the support member so as to extend to both left and right sides such that the press member is configured to wrap a pelvis of a user, wherein the press member is configured with first and second belt members that have elasticity in a longitudinal direction wherein the first and second belt members are placed respectively in upper and lower portions of the support member such that central parts thereof are attached to the support member wherein the second belt member has a width in a width direction, which is perpendicular to the longitudinal direction, and the upper portion and the lower portion of the support member are separated vertically by a gap of about the width of the second belt member, distal ends of the first and second belt members are united, and coupling parts are placed at the distal ends of the first and second belt members, the first and second belt members configured to press the pelvis with elastic forces when having the support member contact with a rear side of the pelvis, which corresponds to a backbone of the user, and when in use coupling the coupling parts of the press member on a front side of the pelvis, wherein the coupling parts are configured to be coupled by overlapping one another, and one of the coupling parts that is positioned above the other of the coupling parts is defined as a front coupling part, and a surface of the front coupling part that is configured to not face the user is defined as a front surface of the front coupling part, the pelvis correction belt is further provided with a first pressing auxiliary belt and a second pressing auxiliary belt, each of which having a distal end and a base end wherein the distal end is a free tip not fixed to any portion of the pelvis correction belt and has a combining part when the pelvis correction belt wraps the hip, the base end of the first pressing auxiliary belt is attached to the upper portion of the support member so as to be configured to extend from the support member to the left of the user, the base end of the second pressing auxiliary belt is attached to the lower portion of the support member so as to extend from the support member to the right of the user, and by combining the combining parts of the first pressing auxiliary belt and the second pressing auxiliary belt both with the front surface of the front coupling part, the first pressing auxiliary belt is configured to press presses an upper-left portion on the rear side of the pelvis through the first belt member, and the second pressing auxiliary belt is configured to press presses a lower-right portion on the rear side of the pelvis through the second belt member.

9. The pelvis correction belt according to claim 8, wherein
a pressing force by the second pressing auxiliary belt is greater than a pressing force by the first pressing auxiliary belt.

10. The pelvis correction belt according to claim 9, wherein
the second belt member of the press member is provided with a wide protective part on a portion where the second belt member of the belt members is configured to be in contact with the lower-right portion on the rear side of the pelvis, and the second pressing auxiliary belt presses the pelvis through the protective part.

11. The pelvis correction belt according to claim 8, wherein
the combining parts of the first pressing auxiliary belt and the second pressing auxiliary belt are combined with the front surface of the front coupling part using hook and loop fasteners, and
the front surface of the front coupling part has one type selected either from the hook fastener or the loop fastener, and
the combining parts of the first pressing auxiliary belt and the second pressing auxiliary belt both have the other type of the hook and loop fasteners, different from the front surface of the front coupling part.

12. The pelvis correction belt according to claim 11, wherein the coupling parts of the first and second belt members are coupled using hook and loop fasteners, wherein the coupling part that is positioned behind the front coupling part is defined as a back coupling part, and a surface of the back coupling part that is configured to not face the user is defined a front surface of the back coupling part, the front surface of the back coupling part has the same type of the hook and loop fasteners as the front surface of the front coupling part such that the combining parts of the first pressing auxiliary belt and the second pressing auxiliary belt are able to be combined with the front surface of the back coupling part as well as the front coupling part.

13. The pelvis correction belt according to claim 8, wherein
the second belt member of the press member is provided with a wide protective part on a portion where the second belt member of the belt members is configured to be in contact with the lower-right portion on the rear side of the pelvis, and
the second pressing auxiliary belt presses the pelvis through the protective part.

14. The pelvis correction belt according to claim 8, wherein
the first belt member has the same width as the second belt member.

* * * * *